(12) United States Patent
Hsiung et al.

(10) Patent No.: US 12,347,566 B2
(45) Date of Patent: Jul. 1, 2025

(54) BLOOD PRESSURE ESTIMATION WITH PHOTOPLETHYSMOGRAPHY MEASUREMENT

(71) Applicant: VIAVI Solutions Inc., San Jose, CA (US)

(72) Inventors: Chang Meng Hsiung, Redwood City, CA (US); Lan Sun, Santa Rosa, CA (US)

(73) Assignee: VIAVI Solutions Inc., Chandler, AZ (US)

(*) Notice: Subject to any disclaimer, the term of this patent is extended or adjusted under 35 U.S.C. 154(b) by 941 days.

(21) Appl. No.: 16/859,568

(22) Filed: Apr. 27, 2020

(65) Prior Publication Data
US 2021/0335495 A1    Oct. 28, 2021

(51) Int. Cl.
*G16H 50/50*    (2018.01)
*G06F 17/17*    (2006.01)

(52) U.S. Cl.
CPC ............. *G16H 50/50* (2018.01); *G06F 17/17* (2013.01)

(58) Field of Classification Search
CPC ........ G16H 50/50; G16H 50/20; G06F 17/17; A61B 5/02416; A61B 5/117; A61B 5/681;
(Continued)

(56) References Cited

U.S. PATENT DOCUMENTS

2003/0176796 A1* 9/2003 Lin ..................... B42D 15/00
                                                         600/485
2015/0065826 A1    3/2015 Mulligan et al.
(Continued)

FOREIGN PATENT DOCUMENTS

CN    105361869 A    3/2016
CN    108403101 A    8/2018
(Continued)

OTHER PUBLICATIONS

Zhang et al., Motion Artifact Reduction for Wrist-Worn Photoplethysmograph Sensors Based on Different Wavelengths, 2019, Sensors, pp. 1-18 (Year: 2019).*

(Continued)

*Primary Examiner* — Ryan F Pitaro
*Assistant Examiner* — Bernard E Cothran
(74) *Attorney, Agent, or Firm* — FOLEY & LARDNER LLP

(57) ABSTRACT

A device may obtain a heartbeat profile of a current subject, the heartbeat profile being based on photoplethysmography (PPG) data associated with a set of wavelength channels. The device may determine a global model including a plurality of classes, each associated with a subject identifier and a blood pressure level (BPL) identifier. The device may identify a class as a closest class to the current subject based on the heartbeat profile of the current subject. The device may identify a local subject associated with the closest class based on the subject identifier associated with the closest class. The device may generate a BPL estimation model for the current subject based on heartbeat profile data for the local subject. The device may determine a BPL estimation for the current subject based on the heartbeat profile of the current subject and using the BPL estimation model.

20 Claims, 9 Drawing Sheets

(58) Field of Classification Search
CPC ... A61B 5/7267; A61B 5/021; A61B 5/02108; A61B 5/02433; A61B 5/02438; A61B 5/7264; A61B 5/7275
See application file for complete search history.

(56) References Cited

U.S. PATENT DOCUMENTS

| | | | |
|---|---|---|---|
| 2016/0038044 A1 | 2/2016 | Banerjee et al. | |
| 2017/0135591 A1* | 5/2017 | Ishizawa | A61B 5/7235 |
| 2018/0136193 A1* | 5/2018 | Messerschmidt | A61B 5/021 |
| 2019/0175042 A1* | 6/2019 | Wang | A61B 5/7278 |
| 2019/0298195 A1* | 10/2019 | De Groot | A61B 5/7264 |
| 2019/0365254 A1* | 12/2019 | Chen | A61B 5/02255 |
| 2020/0113527 A1 | 4/2020 | Park et al. | |

FOREIGN PATENT DOCUMENTS

| | | |
|---|---|---|
| CN | 111012323 A | 4/2020 |
| EP | 3033991 A1 | 6/2016 |
| EP | 3636146 A1 | 4/2020 |
| WO | 2017096314 A1 | 6/2017 |

OTHER PUBLICATIONS

Visvanathan et al., Estimation of Blood Pressure Levels from Reflective Photoplethysmograph using Smart Phones, 2013, IEEE, pp. 1-5 (Year: 2013).*
Cheng et al., Blood Pressure Tracking Over the Adult Course Patterns and Correlates in the Framingham Heart Study, Dec. 2012, AHA Journals, pp. 1393-1399 (Year: 2012).*
Kryzesinski et al. The diagnostic value of supine blood pressure in hypertension, 2014, AMS, pp. 310-318 (Year: 2014).*
BYJU's, Centroid, 2024, BYJU's, pp. 1-12 (Year: 2024).*
Extended European Search Report for Application No. EP21170300.4, mailed on Sep. 27, 2021, 4 pages.
Extended European Search Report for Application No. EP22205724.2, mailed on Feb. 14, 2023, 7 pages.

* cited by examiner

BLOOD PRESSURE ESTIMATION WITH PHOTOPLETHYSMOGRAPHY MEASUREMENT

BACKGROUND

Photoplethysmography (PPG) is an optical technique that can be used to detect volumetric changes in blood in peripheral circulation (as blood volume changes due to the pumping action of the heart). PPG is a non-invasive method that makes measurements at the surface of the skin (e.g., at a fingertip, a wrist, an ear lobe, and/or the like). A PPG device may take the form of, for example, a multispectral sensor device (e.g., a binary multispectral (BMS) sensor device) that provides heartbeat time-series data associated with multiple wavelength channels (e.g., 64 wavelength channels). The multispectral sensor device may include multiple sensor elements (e.g., optical sensors, spectral sensors, and/or image sensors), each to receive one of the multiple wavelength channels (via a respective region of a multispectral filter) in order to capture the heartbeat time-series data.

SUMMARY

According to some implementations, a method may include obtaining, by a device, a heartbeat profile of a current subject, the heartbeat profile being based on PPG data associated with a set of wavelength channels; determining, by the device, a global model including a plurality of classes, each class of the plurality of classes being associated with a subject identifier and a blood pressure level (BPL) identifier; identifying, by the device, a class, of the plurality of classes included in the global model, as a closest class to the current subject, the closest class being identified based on the heartbeat profile of the current subject; identifying, by the device, a local subject associated with the closest class, the local subject being identified based on the subject identifier associated with the closest class; selecting, by the device, at least two classes, associated with the local subject, to be used for generating a BPL estimation model for the current subject, wherein the at least two classes include the closest class and at least one other class associated with the local subject, the at least one other class being associated with a BPL identifier different from that of the closest class; generating, by the device, the BPL estimation model based on heartbeat profile data for the at least two classes associated with the local subject; and determining, by the device, a BPL estimation for the current subject based on the heartbeat profile of the current subject and using the BPL estimation model.

According to some implementations, a method may include obtaining, by a device, a heartbeat profile of a current subject, the heartbeat profile being based on PPG data associated with a set of wavelength channels; determining, by the device, a global model including a plurality of classes, each class of the plurality of classes being associated with a subject identifier and a BPL identifier; identifying, by the device, a class, of the plurality of classes included in the global model, as a closest class to the current subject, the closest class being identified based on the heartbeat profile of the current subject; identifying, by the device, a local subject associated with the closest class, the local subject being identified based on the subject identifier associated with the closest class; determining, by the device and based on identifying the local subject, a local subject transfer set associated with the local subject, the local subject transfer set including one or more heartbeat profiles of the local subject collected at a reference BPL; obtaining, by the device, a current subject transfer set associated with the current subject, the current subject transfer set including one or more heartbeat profiles of the current subject collected at the reference BPL; creating, by the device, a transferred current subject set based on the current subject transfer set and the local subject transfer set, wherein the transferred current subject set includes a plurality of transferred heartbeat profiles associated with the current subject; generating, by the device, a BPL estimation model based on a local subject set associated with the identified local subject; and determining, by the device, a BPL estimation for the current subject based on the transferred current subject set and using the BPL estimation model.

According to some implementations, a method may include obtaining, by a device, a heartbeat profile of a current subject, the heartbeat profile being based on PPG data associated with a set of wavelength channels; determining, by the device, a global model including a plurality of classes, each class of the plurality of classes being associated with a subject identifier and a BPL identifier; identifying, by the device, a class, of the plurality of classes included in the global model, as a closest class to the current subject, the closest class being identified based on the heartbeat profile of the current subject; identifying, by the device, a local subject associated with the closest class, the local subject being identified based on the subject identifier associated with the closest class; generating, by the device, a BPL estimation model for the current subject based on heartbeat profile data for the local subject; and determining, by the device, a BPL estimation for the current subject based on the heartbeat profile of the current subject and using the BPL estimation model.

DETAILED DESCRIPTION

The following detailed description of example implementations refers to the accompanying drawings. The same reference numbers in different drawings may identify the same or similar elements. Further, while the following description may use a multispectral sensor device in an example, the principles, procedures, operations, techniques, and methods described herein may be used with any other type of sensing device, such as a spectrometer, an optical sensor, a spectral sensor, and/or the like.

As described above, a multispectral sensor device may be capable of measuring, obtaining, collecting, or otherwise determining heartbeat time-series data associated with multiple (e.g., 16, 32, 64, and/or the like) wavelength channels. Such data is herein referred to as PPG data. In some cases, a multispectral sensor device may be used to collect PPG data associated with a subject, and the PPG data may be used to generate a heartbeat profile based on which a blood pressure level (BPL) of the subject can be estimated. However, subject-to-subject variation of PPG-based heartbeat profiles is typical and, even for the same subject, heartbeat profiles can show different variation trends at different regions of BPLs. Therefore, conventional techniques for estimating BPLs based on heartbeat profiles generated from PPG data generally show large bias and poor prediction performance and, thus, are unreliable.

Some implementations described herein provide a device that provides improved PPG-based BPL estimation. In some implementations, the device generates a BPL estimation model for a current subject (i.e., a subject for which a BPL estimation is to be determined) based on heartbeat profile data for a local subject (i.e., a particular subject identified from a global model associated with multiple subjects), and determines a BPL estimation for the current subject based on a heartbeat profile of the current subject and using the BPL estimation model. In some implementations, a manner in which the BPL estimation model is generated may depend on availability of heartbeat profile data for the current subject and/or of heartbeat profile data for global subjects associated with the global model. Various techniques for generating the BPL estimation model are provided below.

Figure 1A:
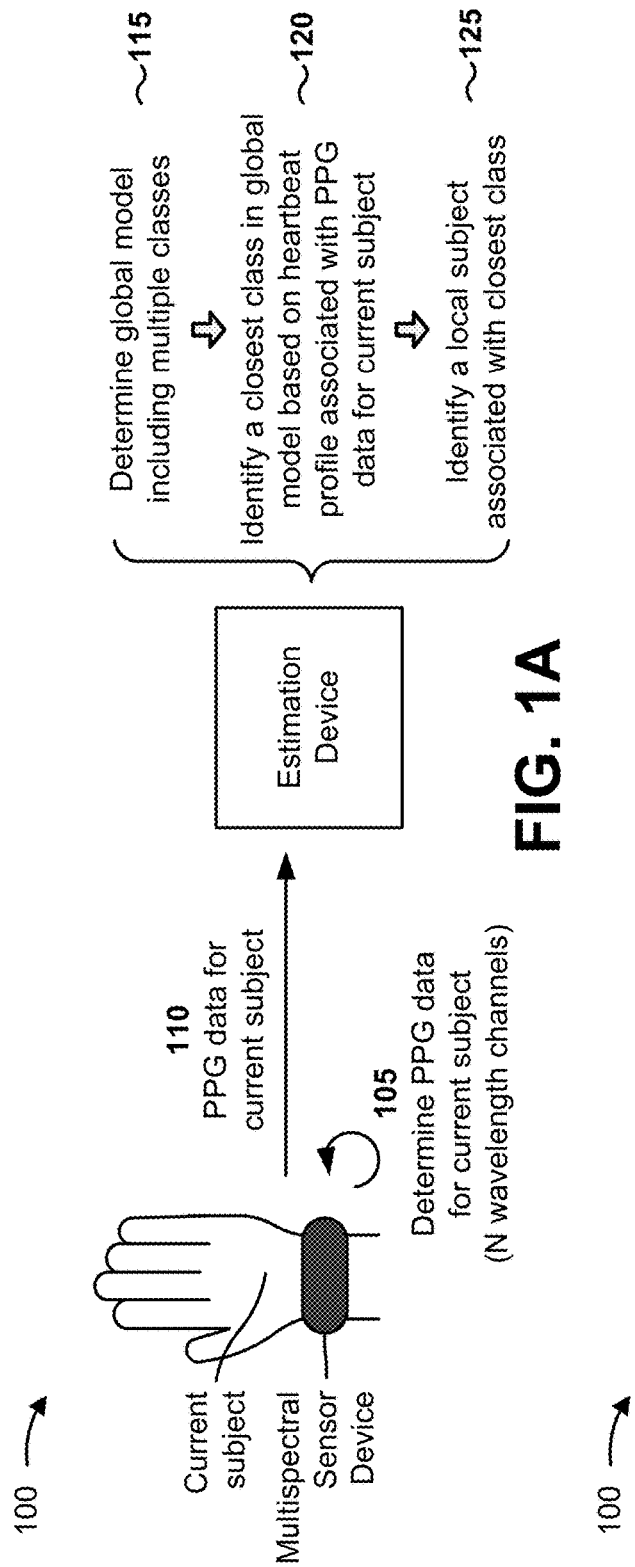
FIGS. 1A and 1B are diagrams of an example implementation described herein.
Figure 1B:
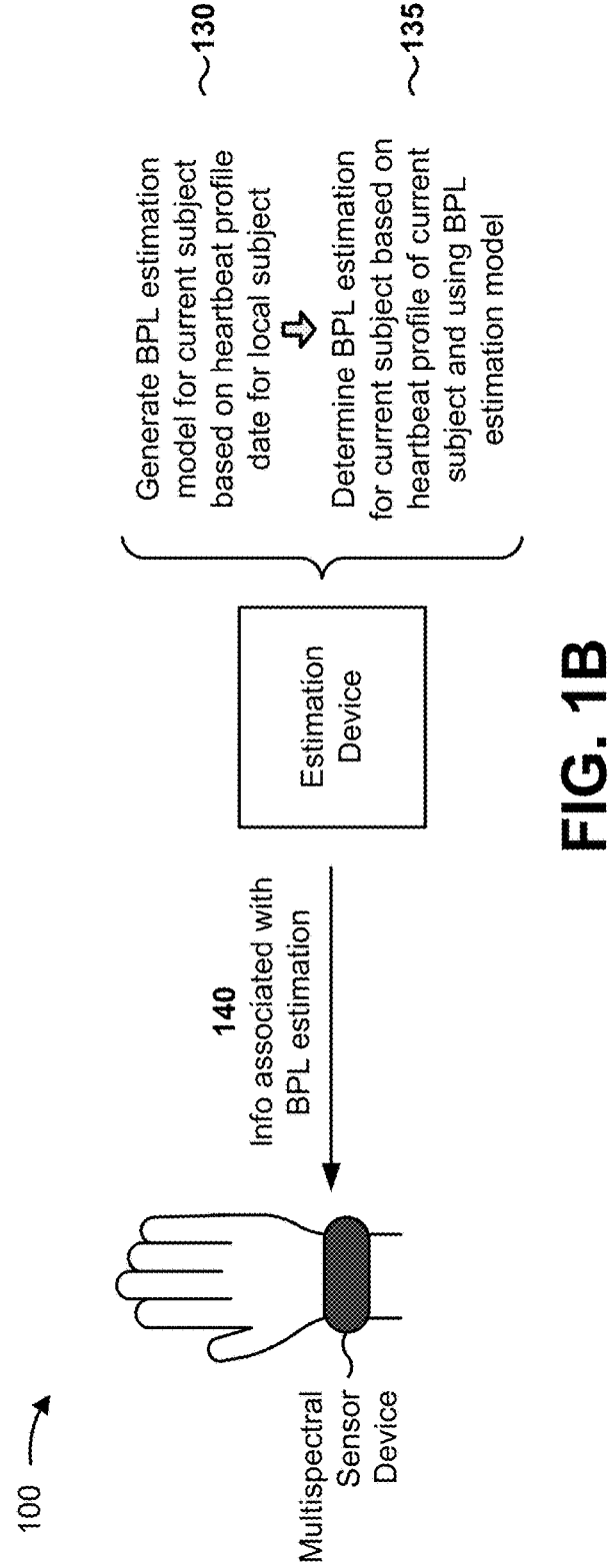

FIGS. 1A and 1B are diagrams of an example implementation 100 described herein.

As shown in FIG. 1A, a multispectral sensor device may be positioned relative to a skin surface of a current subject (i.e., a subject for which a BPL estimation is to be determined). For example, as shown in FIG. 1A, the multispectral sensor device may be a device worn on the wrist of the current subject. In some implementations, the multispectral sensor device may be positioned relative to the skin surface at another location on the body, such as on a fingertip, an arm, a leg, an ear lobe, and/or the like. In some implementations, the multispectral sensor device includes a BMS sensing device that operates in, for example, the visible (VIS) spectrum, the near infrared (NIR) spectrum, and/or the like.

As shown by reference 105, the multispectral sensor device may determine (e.g., measure, gather, collect, and/or the like) PPG data (e.g., raw heartbeat data) associated with N (N>1) wavelength channels. The PPG data includes, for each of the N wavelength channels, photometric response data that indicates a blood volume beneath the skin surface at the location of the multispectral sensor device at a given time point.

As shown by reference number 110, an estimation device may obtain the PPG data from the multispectral sensor device. The estimation device is a device capable of generating a BPL estimation model associated with the current subject and/or determining a BPL estimation for the current subject using the BPL estimation model, as described herein. In some implementations, the estimation device may be integrated with the multispectral sensor device (e.g., in a same package, a same housing, on a same chip, and/or the like). Alternatively, the estimation device may be separate (e.g., remotely located) from the multispectral sensor device.

In some implementations, the estimation device may obtain the PPG data in real-time or near real-time (e.g., when the multispectral sensor device is configured to provide the PPG data as the multispectral sensor device obtains the PPG data). Additionally, or alternatively, the estimation device may obtain the PPG data based on the multispectral sensor device (e.g., automatically) providing the PPG data on a periodic basis (e.g., every one second, every five seconds, and/or the like). Additionally, or alternatively, the estimation device may obtain the PPG data from the multispectral sensor device based on requesting the PPG data from the multispectral sensor device.

As shown by reference 115, the estimation device may determine a global model including a plurality of classes. In some implementations, one or more classes of the global model may be used as a basis for generating the BPL estimation model, as described below. In some implementations, each class of the global model includes heartbeat profile data associated with a subject identifier and a BPL identifier. That is, each class may be associated with a subject identifier corresponding to a local subject (e.g., a subject for which a set of heartbeat profiles have been collected, each at a respective known BPL) of a group of local subjects, and a BPL identifier indicating a BPL at which the associated heartbeat profile data was collected. In some implementations, as described below, the estimation device identifies a closest class to the current subject based on the global model, and generates a BPL estimation model for the current subject based on heartbeat profile data for a local subject associated with the identified closest class.

In some implementations, the estimation device may generate the global model. For example, the estimation device may obtain heartbeat profiles associated with a group of local subjects, where each heartbeat profile is a heartbeat profile of one of the local subjects and is associated with a respective known BPL. As a particular example, the estimation device may obtain a first group of heartbeat profiles associated with a first local subject and a second group of heartbeat profiles associated with a second local subject. Here, a first heartbeat profile in the first group of heartbeat profiles may be associated with (e.g., have been collected at) a first known BPL of the first local subject, a second heartbeat profile in the first group of heartbeat profiles may be associated with a second known BPL of the first local subject, and so on. Thus, the first group of heartbeat profiles may include a group of heartbeat profiles of the first local subject, each of which is associated with a respective known BPL of the first local subject. Similarly, a first heartbeat profile in the second group of heartbeat profiles may be associated with a first known BPL of the second local subject, a second heartbeat profile in the second group of heartbeat profiles may be associated with a second known BPL of the second local subject, and so on. Thus, the second group of heartbeat profiles may include a group of heartbeat profiles of the second local subject, each of which is associated with a respective known BPL of the second local subject. Groups of heartbeat profiles associated with other local subjects may include similar information. In some implementations, the estimation device obtains the heartbeat profiles associated with the group of local subjects from another device (e.g., a device configured with a database that stores heartbeat profiles for subjects that are collected at known BPLs).

In some implementations, the group of heartbeat profiles for a given local subject may include one or more heartbeat profiles collected at a reference BPL (e.g., as measured by a reference blood pressure monitor, such as a clinically approved blood pressure monitor, a home-use blood pressure monitor, or the like). In some implementations, the group of heartbeat profiles for the given local subject may include at least one additional heartbeat profile collected at a BPL that differs from the reference BPL by at least a particular amount (e.g., 20 millimeters-mercury (mmHg)). In some implementations, the group of heartbeat profiles for the given local subject includes heartbeat profiles associated with at least two BPLs: one or more heartbeat profiles associated with the reference BPL and one or more heartbeat profiles associated with a BPL that differs from the reference BPL (e.g., by a particular amount).

In some implementations, the estimation device generates the global model based on the heartbeat profiles associated with the group of local subjects. For example, the estimation device may generate the global model to include a plurality of classes. Here, a first class may correspond to a heartbeat profile associated with a first local subject and a first known BPL, a second class may correspond to a heartbeat profile associated with the first local subject and a second known BPL, a third class may correspond to a heartbeat profile associated with the first local subject and a third known BPL, a fourth class may correspond to a heartbeat profile associated with a second local subject and a fourth known BPL, a fifth class may correspond to a heartbeat profile associated with the second local subject and a fifth known BPL, a sixth class may correspond to a heartbeat profile associated with a third local subject and a sixth known BPL, a seventh class may correspond to a heartbeat profile associated with the third local subject and a seventh known BPL, and so on for each heartbeat profile in the group of heartbeat profiles. In general, in the global model, each heartbeat profile for each local subject at each BPL is treated as one class (e.g., such that a multi-label all combinations classification is performed to generate the global model). In some implementations, the estimation device may generate the global model using a non-linear classifier, such as a support vector machine (SVM) classifier or a hierarchical SVM classifier (ILM).

In some implementations, the estimation device may store the global model (e.g., such that the global model can be used to generate a BPL estimation model at a later time). Additionally, or alternatively, the estimation device may determine the global model based on receiving the global model from another device (e.g., when the estimation device is not configured to generate the global model).

Figure 2:
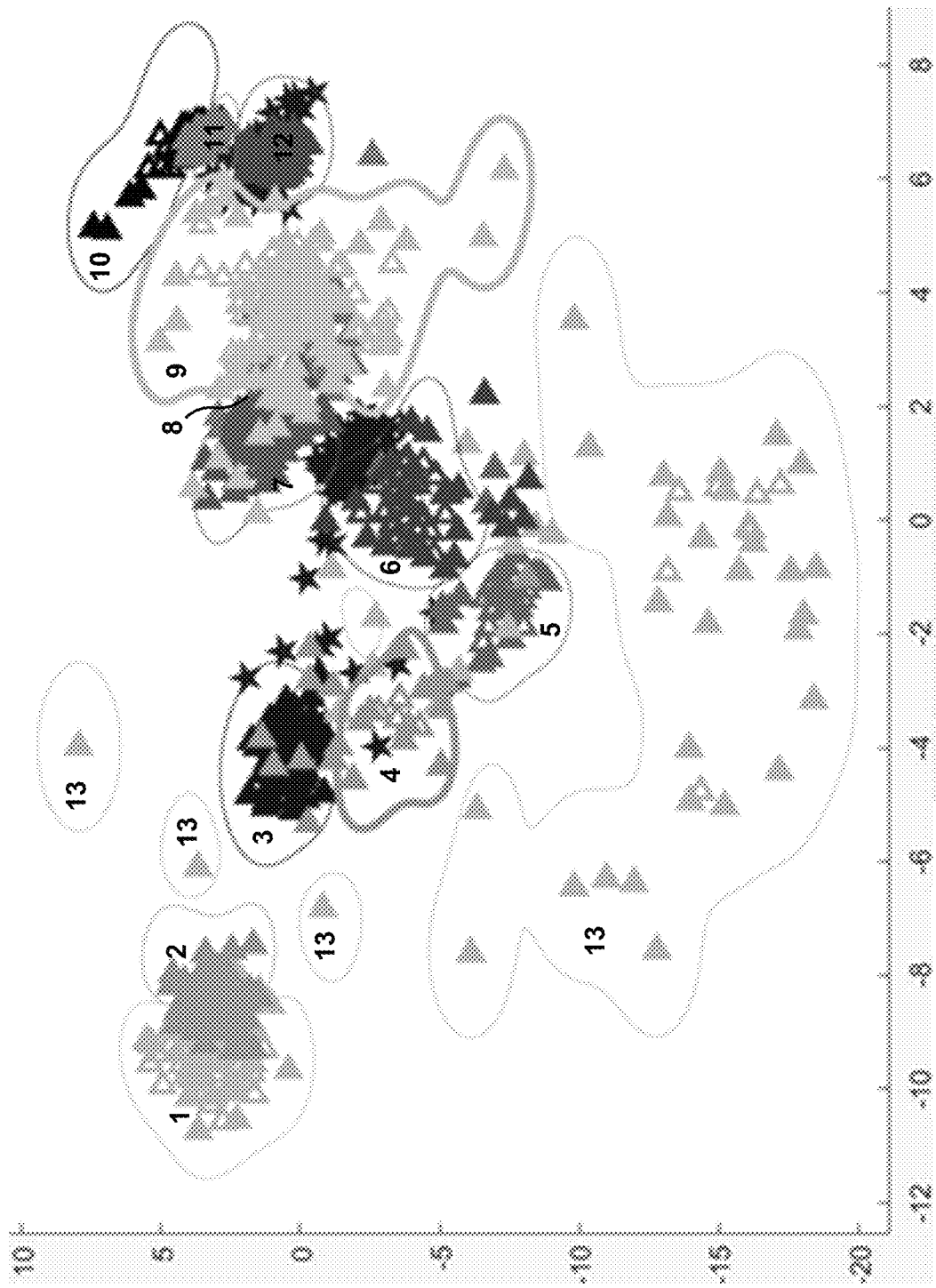
FIG. 2 is a diagram of an example associated with a global model associated with a plurality of classes, as described herein.

FIG. 2 is a diagram illustrating an example of a global model in which each BPL for each local subject is treated as different class in the global model, as described above. In the example shown in FIG. 2, there are 13 classes (as labeled in FIG. 2) associated with five local subjects. Here, each region indicated in FIG. 2 is associated with one of the 13 classes, where each class corresponds to a different local subject identifier and BPL combination. Notably, identification of points within individual regions is not necessary for understanding the concept illustrated by FIG. 2; consequently, clear delineation of each point is not shown in FIG. 2. Further, FIG. 2 is provided merely as an example. Other examples may differ from what is described with regard to FIG. 2.

Returning to FIG. 1A, as shown by reference 120, the estimation device may identify a class, of the plurality of classes included in the global model, as a closest class to the current subject. In some implementations, the estimation device may identify the closest class based on the heartbeat profile of the current subject. For example, the estimation device may classify the heartbeat profile for the current subject to one of the classes included in the global model. Here, the class of the global model to which the heartbeat profile of the current subject is classified may be identified as the closest class. In some implementations, the estimation device may use pattern matching to identify the closest class.

As shown by reference 125, the estimation device may identify a local subject associated with the closest class. In some implementations, the local subject is identified based on the subject identifier associated with the closest class. For example, the estimation device may identify the closest class to the current subject, as described above. Here, since each class of the global model is associated with a subject identifier, the estimation device may identify the local subject associated with the closest class based on the subject identifier of the closest class.

As shown by reference 130 in FIG. 1B, the estimation device may generate a BPL estimation model for the current subject based on heartbeat profile data for the local subject associated with the closest class (herein referred to as the identified local subject).

In some implementations, when generating the BPL estimation model, the estimation device may select at least two classes associated with the identified local subject, and generate the BPL estimation model based on heartbeat profile data for the at least two classes associated with the identified local subject. In some implementations, the at least two classes may include the closest class and at least one other class associated with the identified local subject (e.g., at least one other class associated with a BPL identifier that is different from a BPL identifier of the closest class). In some implementations, when selecting the at least two classes, the estimation device may identify a linear region of a set of classes associated with the identified local subject, and select the at least two classes based on the linear region of the set of classes associated with the identified local subject. Thus, in some implementations, a linear region of the identified local subject may be used in association with generating in-situ a BPL estimation model (e.g., a local regression model) that can be used to estimate a BPL of the current subject.

Figure 3:
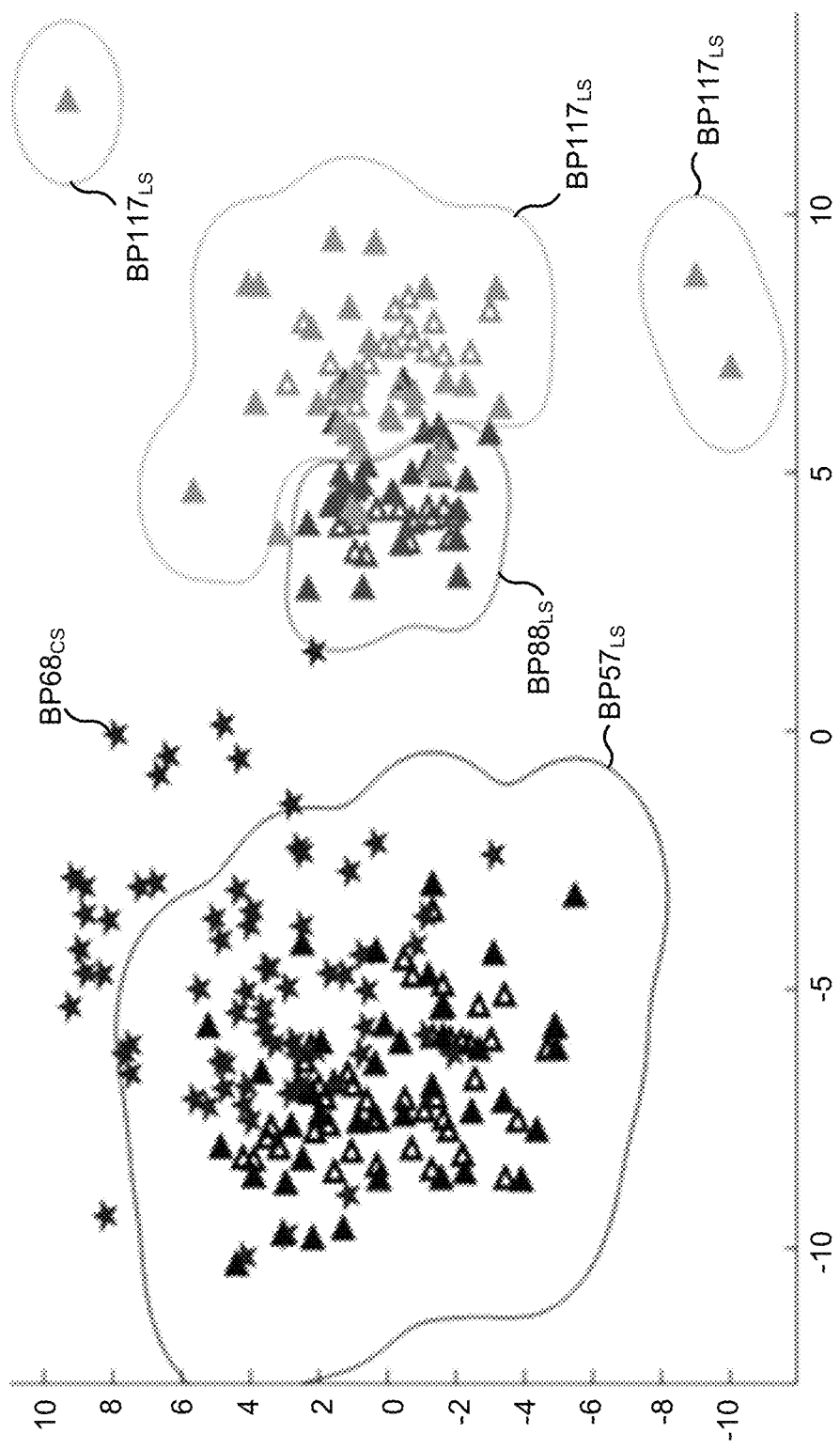
FIGS. 3 and 4 are diagrams illustrating examples associated with identification of a closest class based on heartbeat profile data associated with a current subject, as described herein.
Figure 4:
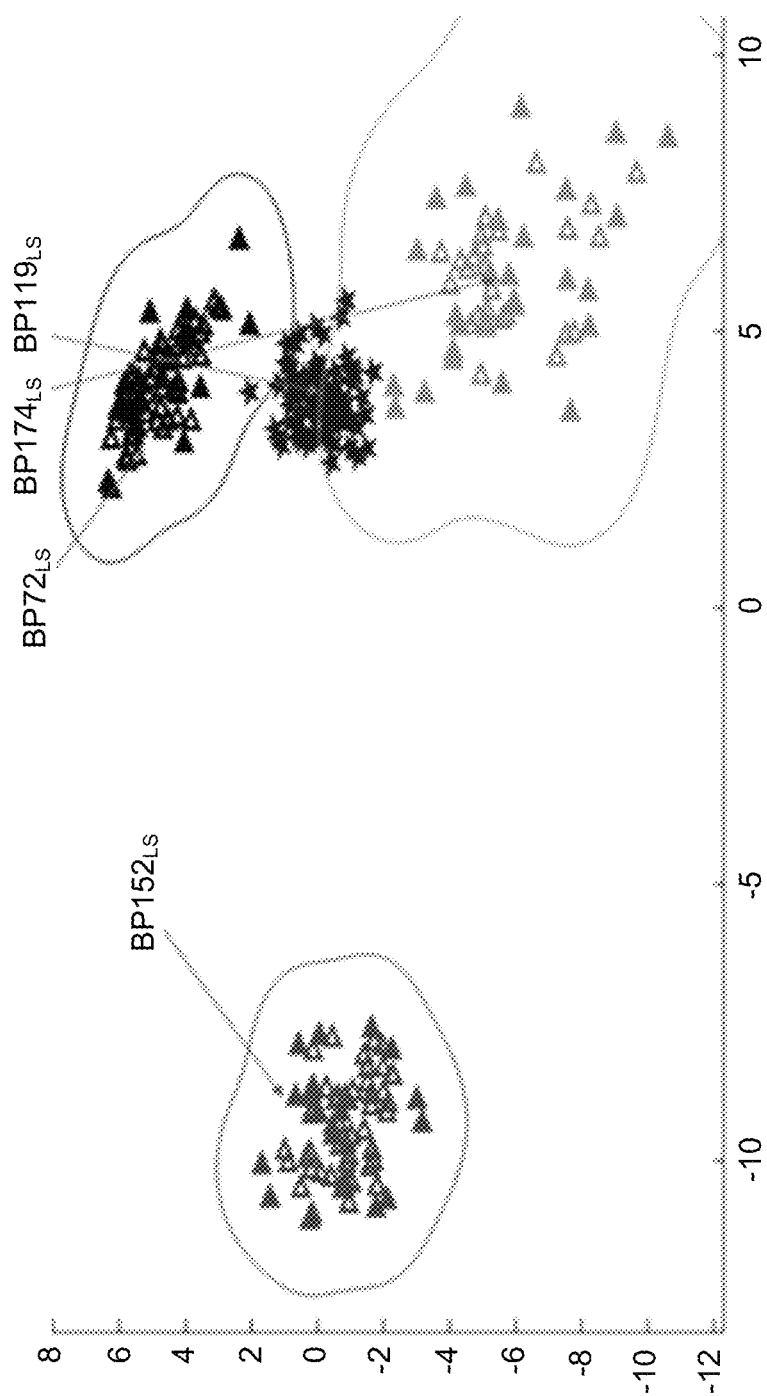

In practice, heartbeat profiles of different current subjects can result in selection of different combinations of classes being selected as a basis for generating the BPL estimation model, depending on a location and a classifier used. FIG. 3 shows an example associated with a validation set of data of an example current subject shown within an identified local subject's PCA-SVM plot. Here, it can be seen that unknown spectra of the heartbeat profile data of the current subject (identified by the star symbols labeled $BP68_{CS}$ in FIG. 3) are located between a first class associated with a first BPL of the local subject (identified by region $BP57_{LS}$ in FIG. 3) and a second class associated with a second BPL of the local subject (identified by region $BP88_{LS}$ in FIG. 3) or a third class associated with a third BPL of the local subject (identified by region $BP117_{LS}$ in FIG. 3). In this example, 57 out of 70 samples associated with the current subject select the first and second classes as the two classes based on which to generate the BPL estimation model, and 13 out of 70 samples select the first and third classes as the two classes based on which to generate the BPL estimation model. Notably, in some scenarios, the two classes may not be the two classes associated with BPLs that are closest to the BPL of the current subject, an example of which is illustrated in FIG. 4. In FIG. 4, unknown spectra of the heartbeat profile data of the current subject (identified by the star symbols labeled $BP119_{CS}$ in FIG. 4) are located between a first class associated with a first BPL of the local subject (identified by region $BP72_{LS}$ in FIG. 4) and a second class associated with a second BPL of the local subject (identified by region BP152$_{LS}$ in FIG. 4) or a third class associated with a third BPL of the local subject (identified by region BP174$_{LS}$ in FIG. 4). In this example, some samples associated with the current subject select the first and third classes as the two classes (despite the second class having a BPL that is closer to the actual BPL of the current subject than either the first or third class). In some implementations, such selection is a result of a class behaving non-linearly with respect to other classes in the x-matrix space. As indicated above, FIGS. 3 and 4 are provided merely as examples. Other examples may differ from what is described with regard to FIGS. 3 and 4.

In some implementations, as noted above, the estimation device may generate the BPL estimation model based on heartbeat profile data for the at least two classes associated with the local subject. For example, the estimation device may obtain the heartbeat profile data associated with the at least two classes, and may generate a local regression model based on the heartbeat profile data. In some implementations, the BPL estimation model generated based on the heartbeat profile data associated with the at least two classes may be a quantitative model that is generated using partial least squares regression. In some implementations, a BPL estimation provided by such a BPL estimation model may include an estimated BPL of the current subject (e.g., a quantitative estimation of the BPL of the current subject). In some implementations, the BPL estimation may be a qualitative BPL estimation (e.g., an indication of whether the BPL of the current subject has increased, decreased, or is unchanged, or an indication of whether the current subject is in hypotension, a normal state, prehypertension, hypertension stage 1, hypertension stage 2, or a hypertensive crisis).

In some implementations, a signal point calibration (SPC) usage model may be used in association with generating the BPL estimation model. Here, to generate the BPL estimation model, the estimation device may determine a local subject transfer set associated with the identified local subject. The local subject transfer set may include one or more heartbeat profiles of the identified local subject that were collected at a reference BPL. Next, the estimation device may obtain a current subject transfer set associated with the current subject. The current subject transfer set may include one or more heartbeat profiles of the current subject collected at the reference BPL. According to the SPC usage model, PPG signals should be (previously) collected for the current subject at one or more known BPLs to provide a group of heartbeat profiles associated with the current subject. This group of heartbeat profiles can then be used to perform a model transfer that can reduce bias associated with cross-subject model predictions. In some implementations, the group of heartbeat profiles for the current subject may include one or more heartbeat profile collected at a reference BPL (e.g., as measured by a reference blood pressure monitor, such as a clinically approved blood pressure monitor, a home-use blood pressure monitor, or the like). In some implementations, the group of heartbeat profiles for the current subject includes heartbeat profiles associated with two or more BPLs: one or more heartbeat profiles associated with the reference BPL and one or more heartbeat profiles associated with a BPL that differs from the reference BPL (e.g., by a particular amount).

In some implementations, the estimation device may create a transferred current subject set based on the current subject transfer set and the local subject transfer set. The transferred current subject set may include a plurality of transferred heartbeat profiles associated with the current subject. As an example, the estimation device may create the transferred current subject set using mean difference correction (MDC). According to MDC, a centroid of the current subject transfer set can be mapped to a centroid of the local subject transfer set. Here, when the centroids are mapped to the same location, bias may be removed. A result of the mapping is the transferred current subject transfer set. In some implementations, the estimation device may create the transferred current subject using, for example, MDC, piecewise direct standardization, generalized least squares, orthogonal signal correction, or another technique. Notably, in some cases, the BPL estimation model may be used to provide a categorical output (rather than an estimated BPL value).

Next, the estimation device may generate the BPL estimation model based on a local subject set associated with the identified local subject (e.g., a linear region of a set of heartbeat profiles of the local subject). For example, the estimation device may generate the BPL estimation model based on the local subject set using linear regression. In some implementations, the BPL estimation model generated based on a local subject set associated with the identified local subject may be a quantitative model that is generated using partial least squares regression. In some implementations, a BPL estimation provided by such a BPL estimation model may include an estimated BPL of the current subject (e.g., a quantitative estimation of the BPL of the current subject). In some implementations, the BPL estimation model generated based on a local subject set associated with the identified local subject may be a qualitative model generated using a classifier. In some implementations, a BPL estimation provided by such a BPL estimation model may include a categorical output associated with the current subject, such as an indication of whether the BPL of the current subject has increased, decreased, or is unchanged, or an indication of whether the current subject is in a particular state (e.g., hypotension, normal, prehypertension, hypertension stage 1, hypertension stage 2, a hypertensive crisis or the like).

As shown by reference 130 in FIG. 1B, the estimation device may determine a BPL estimation for the current subject based on the transferred current subject set and using the BPL estimation model. For example, the estimation device may provide information associated with the transferred current subject set (e.g., information associated with one or more transferred heartbeat profiles of the current subject) as input to the BPL estimation model and may receive, as an output, the BPL estimation associated with the current subject. In some implementations, as described above, the BPL estimation may be a quantitative BPL estimation (e.g., an estimated BPL) or a qualitative BPL estimation (e.g., an indication of whether the BPL of the current subject has increased, decreased, or is unchanged, or an indication of whether the current subject is in hypotension, a normal state, prehypertension, hypertension stage 1, hypertension stage 2, or a hypertensive crisis).

As shown by reference 135, the estimation device may provide information associated with the BPL estimation of the current subject. For example, in some implementations, the estimation device may provide information associated with the BPL estimation for display (e.g., via a display screen of the multispectral sensor device, via a display screen of the monitoring device, and/or the like).

In some implementations, the estimation device may repeat the above described process (e.g., automatically on a periodic basis, based on an indication of a user, and/or the like) in order to enable monitoring of a BPL of the current subject (e.g., in real-time or near real-time).

In this way, an estimation device can non-invasively estimate and/or monitor a BPL of a current subject based on heartbeat profiles generated by PPG signals (e.g., based on full spectrum NIR). In some cases, beat-by-beat blood pressure monitoring can be performed. Notably, the above-described techniques can be used with both single-channel PPG and multi-channel PPG.

As indicated above, FIGS. 1A and 1B are provided merely as examples. Other examples may differ from what is described with regard to FIGS. 1A and 1B.

Figure 5:
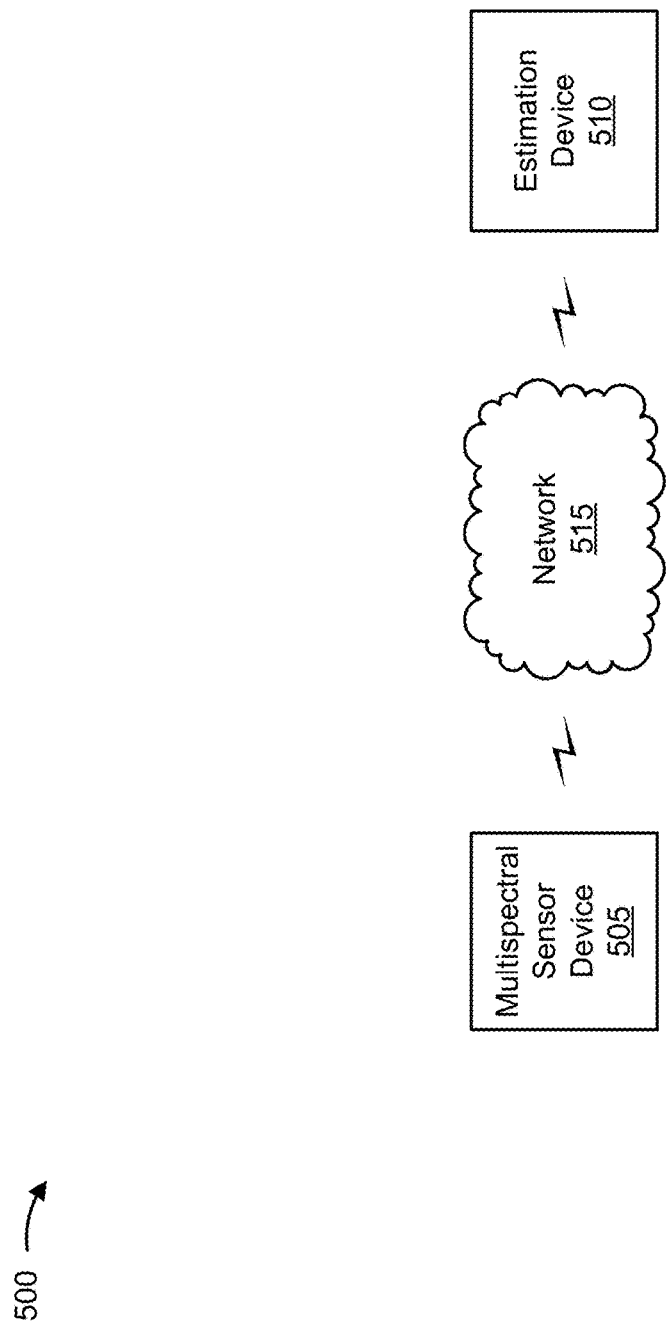
FIG. 5 is a diagram of an example environment in which systems and/or methods described herein may be implemented.

FIG. 5 is a diagram of an example environment 500 in which systems and/or methods described herein may be implemented. As shown in FIG. 5, environment 500 may include a multispectral sensor device 505, an estimation device 510, and a network 515. Devices of environment 500 may interconnect via wired connections, wireless connections, or a combination of wired and wireless connections. Multispectral sensor device 505 and estimation device 510 may correspond to the multispectral sensor device and the estimation device, respectively, described above in association with FIGS. 1A and 1B.

Multispectral sensor device 505 includes a device capable of measuring, gathering, collecting, or otherwise determining PPG data associated with a plurality of wavelength channels, as described herein. For example, multispectral sensor device 505 may include a multispectral sensing device capable of determining PPG data (in the form of multivariate time-series data) on each of 64 wavelength channels. In some implementations, multispectral sensor device 505 may operate in the visible spectrum, the near infrared spectrum, the infrared spectrum, and/or the like. In some implementations, multispectral sensor device 505 may be a wearable device (e.g., a device worn that can be worn on a wrist, a finger, an arm, a leg, a head, an ear, and/or the like). In some implementations, multispectral sensor device 505 may be integrated with estimation device 510 (e.g., such that multispectral sensor device 505 and estimation device 510 are on the same chip, in the same package, in the same housing, and/or the like). Alternatively, in some implementations, multispectral sensor device 505 may be separate from estimation device 510. In some implementations, multispectral sensor device 505 may receive information from and/or transmit information to another device in environment 500, such as estimation device 510.

Estimation device 510 includes a device capable of performing one or more operations associated with blood pressure estimation based on PPG data, as described herein. For example, estimation device 510 may include an application specific integrated circuit (ASIC), an integrated circuit, a server, a group of servers, and/or the like, and/or another type of communication and/or computing device. In some implementations, estimation device 510 may be integrated with multispectral sensor device 505 (e.g., such that multispectral sensor device 505 and estimation device 510 are on the same chip, in the same package, in the same housing, and/or the like). Alternatively, in some implementations, estimation device 510 may be separate from multispectral sensor device 505. In some implementations, estimation device 510 may receive information from and/or transmit information to another device in environment 500, such as multispectral sensor device 505.

Network 515 includes one or more wired and/or wireless networks. For example, network 515 may include a wired network (e.g., when multispectral sensor device 505 and estimation device 510 are included in same package and/or a same chip). As another example, network 515 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks. In some implementations, multispectral sensor device 505 and estimation device 510 may communicate wirelessly, such as via Bluetooth, NFC, RF, or the like.

The number and arrangement of devices and networks shown in FIG. 5 are provided as an example. In practice, there may be additional devices and/or networks, fewer devices and/or networks, different devices and/or networks, or differently arranged devices and/or networks than those shown in FIG. 5. Furthermore, two or more devices shown in FIG. 5 may be implemented within a single device, or a single device shown in FIG. 5 may be implemented as multiple, distributed devices. Additionally, or alternatively, a set of devices (e.g., one or more devices) of environment 500 may perform one or more functions described as being performed by another set of devices of environment 500.

Figure 6:
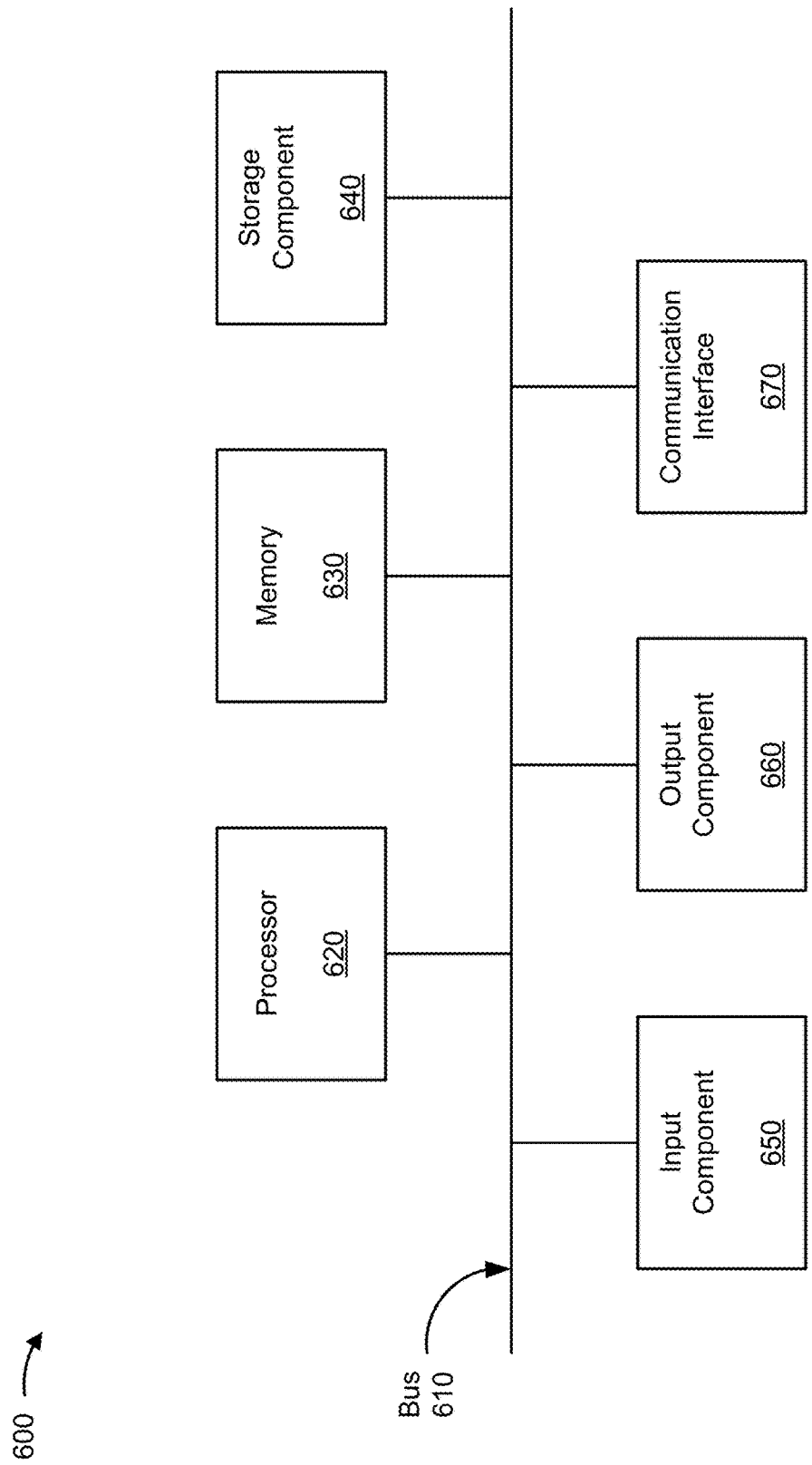
FIG. 6 is a diagram of example components of one or more devices of FIG. 5.

FIG. 6 is a diagram of example components of a device 600. Device 600 may correspond to multispectral sensor device 505 and/or estimation device 510. In some implementations, multispectral sensor device 505 and/or estimation device 510 may include one or more devices 600 and/or one or more components of device 600. As shown in FIG. 6, device 600 may include a bus 610, a processor 620, a memory 630, a storage component 640, an input component 650, an output component 660, and a communication interface 670.

Bus 610 includes a component that permits communication among multiple components of device 600. Processor 620 is implemented in hardware, firmware, and/or a combination of hardware and software. Processor 620 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 620 includes one or more processors capable of being programmed to perform a function. Memory 630 includes a random access memory (RAM), a read only memory (ROM), and/or another type of dynamic or static storage device (e.g., a flash memory, a magnetic memory, and/or an optical memory) that stores information and/or instructions for use by processor 620.

Storage component 640 stores information and/or software related to the operation and use of device 600. For example, storage component 640 may include a hard disk (e.g., a magnetic disk, an optical disk, and/or a magneto-optic disk), a solid state drive (SSD), a compact disc (CD), a digital versatile disc (DVD), a floppy disk, a cartridge, a magnetic tape, and/or another type of non-transitory computer-readable medium, along with a corresponding drive.

Input component 650 includes a component that permits device 600 to receive information, such as via user input (e.g., a touch screen display, a keyboard, a keypad, a mouse, a button, a switch, and/or a microphone). Additionally, or alternatively, input component 650 may include a component for determining location (e.g., a global positioning system (GPS) component) and/or a sensor (e.g., an accelerometer, a gyroscope, an actuator, another type of positional or environmental sensor, and/or the like). Output component 660 includes a component that provides output information from device 600 (via, e.g., a display, a speaker, a haptic feedback component, an audio or visual indicator, and/or the like).

Communication interface 670 includes a transceiver-like component (e.g., a transceiver, a separate receiver, a separate transmitter, and/or the like) that enables device 600 to communicate with other devices, such as via a wired connection, a wireless connection, or a combination of wired and wireless connections. Communication interface 670 may permit device 600 to receive information from another device and/or provide information to another device. For example, communication interface 670 may include an Ethernet interface, an optical interface, a coaxial interface, an infrared interface, a radio frequency (RF) interface, a universal serial bus (USB) interface, a Wi-Fi interface, a cellular network interface, and/or the like.

Device 600 may perform one or more processes described herein. Device 600 may perform these processes based on processor 620 executing software instructions stored by a non-transitory computer-readable medium, such as memory 630 and/or storage component 640. As used herein, the term "computer-readable medium" refers to a non-transitory memory device. A memory device includes memory space within a single physical storage device or memory space spread across multiple physical storage devices.

Software instructions may be read into memory 630 and/or storage component 640 from another computer-readable medium or from another device via communication interface 670. When executed, software instructions stored in memory 630 and/or storage component 640 may cause processor 620 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 6 are provided as an example. In practice, device 600 may include additional components, fewer components, different components, or differently arranged components than those shown in FIG. 6. Additionally, or alternatively, a set of components (e.g., one or more components) of device 600 may perform one or more functions described as being performed by another set of components of device 600.

Figure 7:
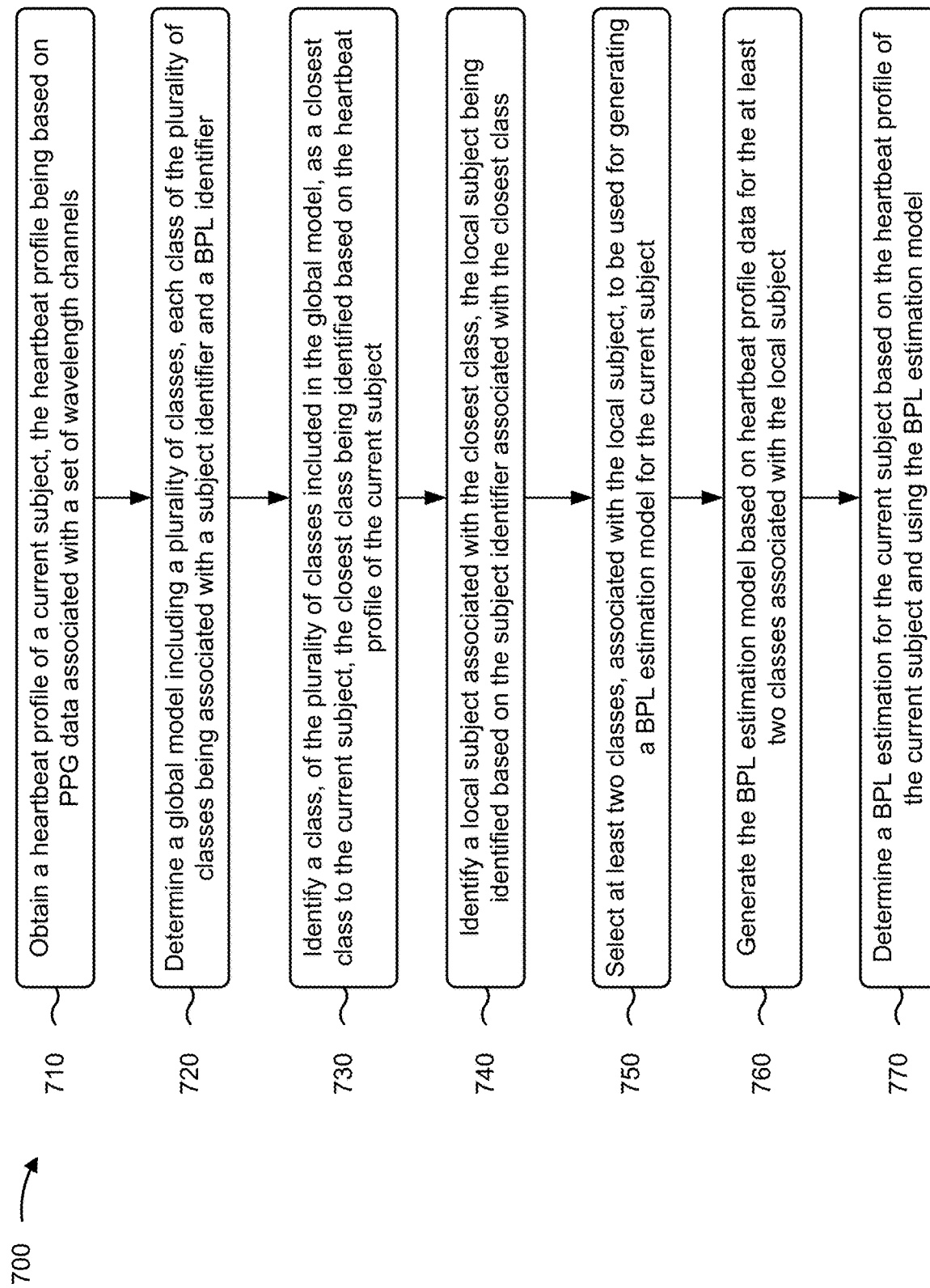
FIGS. 7-9 are flow charts of example processes for determining a blood pressure level estimation based on PPG data, as described herein.

FIG. 7 is a flow chart of an example process 700 for determining a BPL estimation based on PPG data, as described herein. In some implementations, one or more process blocks of FIG. 7 may be performed by an estimation device (e.g., estimation device 510). In some implementations, one or more process blocks of FIG. 7 may be performed by another device or a group of devices separate from or including the estimation device, such as a multi-spectral sensor device (e.g., multispectral sensor device 505).

As shown in FIG. 7, process 700 may include obtaining a heartbeat profile of a current subject, the heartbeat profile being based on PPG data associated with a set of wavelength channels (block 710). For example, the estimation device (e.g., using processor 620, memory 630, storage component 640, input component 650, output component 660, communication interface 670, and/or the like) may obtain a heartbeat profile of a current subject, the heartbeat profile being based on PPG data associated with a set of wavelength channels, as described above.

As further shown in FIG. 7, process 700 may include determining a global model including a plurality of classes, each class of the plurality of classes being associated with a subject identifier and a BPL identifier (block 720). For example, the estimation device (e.g., using processor 620, memory 630, storage component 640, input component 650, output component 660, communication interface 670, and/or the like) may determine a global model including a plurality of classes, each class of the plurality of classes being associated with a subject identifier and a BPL identifier, as described above.

As further shown in FIG. 7, process 700 may include identifying a class, of the plurality of classes included in the global model, as a closest class to the current subject, the closest class being identified based on the heartbeat profile of the current subject (block 730). For example, the estimation device (e.g., using processor 620, memory 630, storage component 640, input component 650, output component 660, communication interface 670, and/or the like) may identify a class, of the plurality of classes included in the global model, as a closest class to the current subject, the closest class being identified based on the heartbeat profile of the current subject, as described above.

As further shown in FIG. 7, process 700 may include identifying a local subject associated with the closest class, the local subject being identified based on the subject identifier associated with the closest class (block 740). For example, the estimation device (e.g., using processor 620, memory 630, storage component 640, input component 650, output component 660, communication interface 670, and/or the like) may identify a local subject associated with the closest class, the local subject being identified based on the subject identifier associated with the closest class, as described above.

As further shown in FIG. 7, process 700 may include selecting at least two classes, associated with the local subject, to be used for generating a BPL estimation model for the current subject (block 750). For example, the estimation device (e.g., using processor 620, memory 630, storage component 640, input component 650, output component 660, communication interface 670, and/or the like) may select at least two classes, associated with the local subject, to be used for generating a BPL estimation model for the current subject, as described above. In some implementations, the at least two classes include the closest class and at least one other class associated with the local subject, the at least one other class being associated with a BPL identifier different from that of the closest class.

As further shown in FIG. 7, process 700 may include generating the BPL estimation model based on heartbeat profile data for the at least two classes associated with the local subject (block 760). For example, the estimation device (e.g., using processor 620, memory 630, storage component 640, input component 650, output component 660, communication interface 670, and/or the like) may generate the BPL estimation model based on heartbeat profile data for the at least two classes associated with the local subject, as described above.

As further shown in FIG. 7, process 700 may include determining a BPL estimation for the current subject based on the heartbeat profile of the current subject and using the BPL estimation model (block 770). For example, the estimation device (e.g., using processor 620, memory 630, storage component 640, input component 650, output component 660, communication interface 670, and/or the like) may determine a BPL estimation for the current subject based on the heartbeat profile of the current subject and using the BPL estimation model, as described above.

Process 700 may include additional implementations, such as any single implementation or any combination of implementations described below and/or in connection with one or more other processes described elsewhere herein.

In some implementations, determining the global model comprises obtaining a plurality of heartbeat profiles associated with a plurality of local subjects, each heartbeat profile of the plurality of heartbeat profiles is a heartbeat profile of one of the plurality of local subjects that is collected at a known BPL, and generating the global model based on the plurality of heartbeat profiles associated with the plurality of local subjects.

In some implementations, the global model is generated using a non-linear classifier.

In some implementations, selecting the at least two classes to be used for generating the BPL estimation model for the current subject comprises identifying a linear region of a set of classes associated with the local subject, the set of classes including the closest class and the at least one other class, and selecting the at least two classes based on the linear region of the set of classes associated with the local subject.

In some implementations, the BPL estimation model is a quantitative model generated using partial least squares regression.

In some implementations, the BPL estimation model is a qualitative model generated using a classifier.

In some implementations, the BPL estimation includes an estimated BPL of the current subject.

In some implementations, process 700 includes providing information associated with the BPL estimation of the current subject.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

Figure 8:
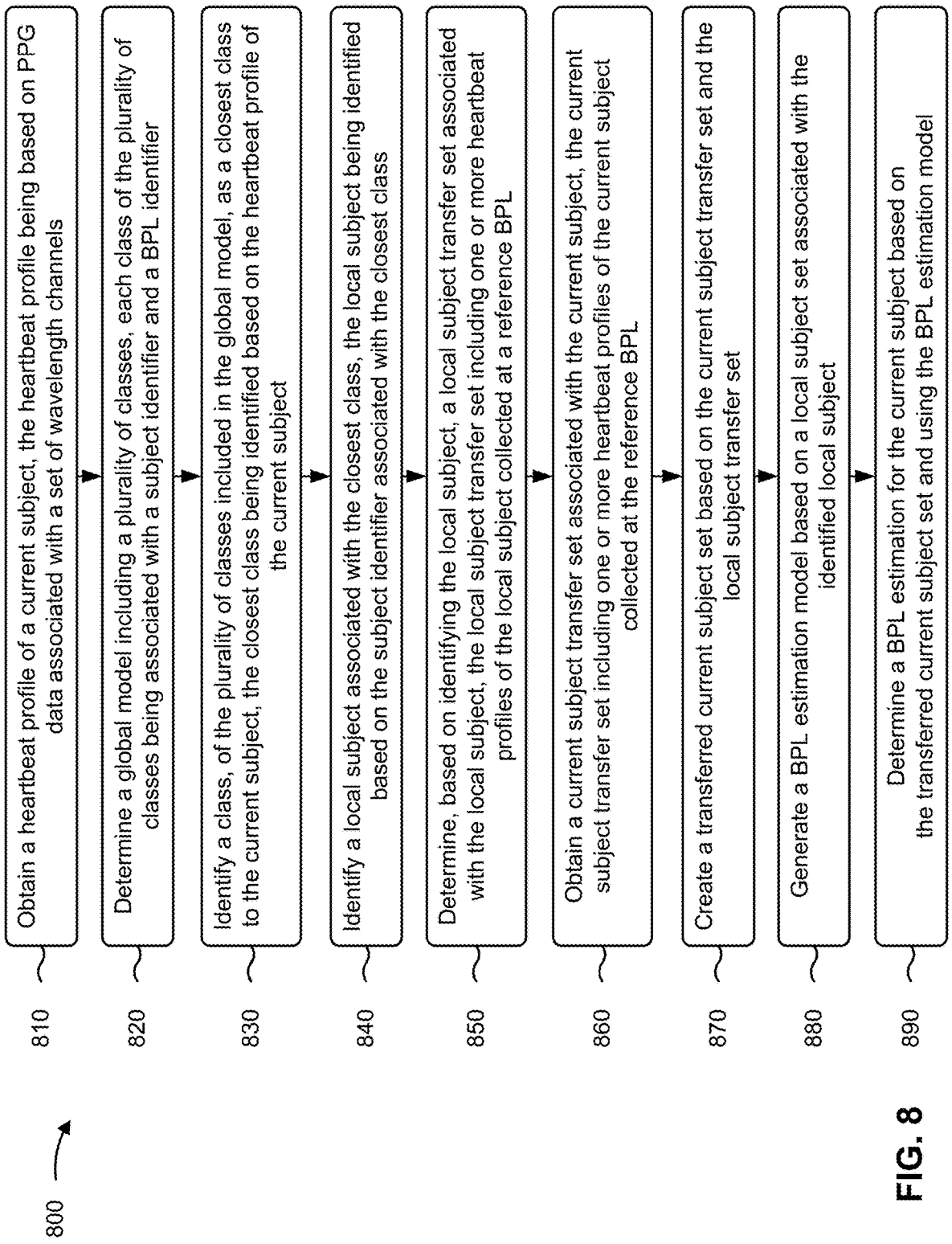

FIG. 8 is a flow chart of an example process 800 for determining a BPL estimation based on PPG data, as described herein. In some implementations, one or more process blocks of FIG. 8 may be performed by an estimation device (e.g., estimation device 510). In some implementations, one or more process blocks of FIG. 8 may be performed by another device or a group of devices separate from or including the estimation device, such as a multispectral sensor device (e.g., multispectral sensor device 505).

As shown in FIG. 8, process 800 may include obtaining a heartbeat profile of a current subject, the heartbeat profile being based on PPG data associated with a set of wavelength channels (block 810). For example, the estimation device (e.g., using processor 620, memory 630, storage component 640, input component 650, output component 660, communication interface 670, and/or the like) may obtain a heartbeat profile of a current subject, the heartbeat profile being based on PPG data associated with a set of wavelength channels, as described above.

As further shown in FIG. 8, process 800 may include determining a global model including a plurality of classes, each class of the plurality of classes being associated with a subject identifier and a BPL identifier (block 820). For example, the estimation device (e.g., using processor 620, memory 630, storage component 640, input component 650, output component 660, communication interface 670, and/or the like) may determine a global model including a plurality of classes, each class of the plurality of classes being associated with a subject identifier and a BPL identifier, as described above.

As further shown in FIG. 8, process 800 may include identifying a class, of the plurality of classes included in the global model, as a closest class to the current subject, the closest class being identified based on the heartbeat profile of the current subject (block 830). For example, the estimation device (e.g., using processor 620, memory 630, storage component 640, input component 650, output component 660, communication interface 670, and/or the like) may identify a class, of the plurality of classes included in the global model, as a closest class to the current subject, the closest class being identified based on the heartbeat profile of the current subject, as described above.

As further shown in FIG. 8, process 800 may include identifying a local subject associated with the closest class, the local subject being identified based on the subject identifier associated with the closest class (block 840). For example, the estimation device (e.g., using processor 620, memory 630, storage component 640, input component 650, output component 660, communication interface 670, and/or the like) may identify a local subject associated with the closest class, the local subject being identified based on the subject identifier associated with the closest class, as described above.

As further shown in FIG. 8, process 800 may include determining, based on identifying the local subject, a local subject transfer set associated with the local subject, the local subject transfer set including one or more heartbeat profiles of the local subject collected at a reference BPL (block 850). For example, the estimation device (e.g., using processor 620, memory 630, storage component 640, input component 650, output component 660, communication interface 670, and/or the like) may determine, based on identifying the local subject, a local subject transfer set associated with the local subject, the local subject transfer set including one or more heartbeat profiles of the local subject collected at or near a reference BPL (e.g., at a BPL or at a BPL closest to a reference BPL), as described above.

As further shown in FIG. 8, process 800 may include obtaining a current subject transfer set associated with the current subject, the current subject transfer set including one or more heartbeat profiles of the current subject collected at the reference BPL (block 860). For example, the estimation device (e.g., using processor 620, memory 630, storage component 640, input component 650, output component 660, communication interface 670, and/or the like) may obtain a current subject transfer set associated with the current subject, the current subject transfer set including one or more heartbeat profiles of the current subject collected at the reference BPL, as described above.

As further shown in FIG. 8, process 800 may include creating a transferred current subject set based on the current subject transfer set and the local subject transfer set (block 870). For example, the estimation device (e.g., using processor 620, memory 630, storage component 640, input component 650, output component 660, communication interface 670, and/or the like) may create a transferred current subject set based on the current subject transfer set and the local subject transfer set, as described above. In some implementations, the transferred current subject set includes a plurality of transferred heartbeat profiles associated with the current subject.

As further shown in FIG. 8, process 800 may include generating a BPL estimation model based on a local subject set associated with the identified local subject (block 880). For example, the estimation device (e.g., using processor 620, memory 630, storage component 640, input component 650, output component 660, communication interface 670, and/or the like) may generate a BPL estimation model based on the local subject set, as described above.

As further shown in FIG. 8, process 800 may include determining a BPL estimation for the current subject based on the transferred current subject set and using the BPL estimation model (block 890). For example, the estimation device (e.g., using processor 620, memory 630, storage component 640, input component 650, output component 660, communication interface 670, and/or the like) may determine a BPL estimation for the current subject based on the transferred current subject set and using the BPL estimation model, as described above.

Process 800 may include additional implementations, such as any single implementation or any combination of implementations described below and/or in connection with one or more other processes described elsewhere herein.

In some implementations, determining the global model comprises obtaining a plurality of heartbeat profiles associated with a plurality of local subjects, where each heartbeat profile of the plurality of heartbeat profiles is a heartbeat profile of one of the plurality of local subjects that is collected at a known BPL, and generating the global model based on the plurality of heartbeat profiles associated with the plurality of local subjects.

In some implementations, the global model is generated using a non-linear classifier.

In some implementations, the transferred current subject set is created using mean difference correction, piecewise direct standardization, generalized least squares, orthogonal signal correction, and/or one or more other calibration transfer methods.

In some implementations, the BPL estimation model is a quantitative model generated using partial least squares regression.

In some implementations, the BPL estimation includes an estimated BPL of the current subject.

In some implementations, the BPL estimation model is a qualitative model generated using a classifier.

In some implementations, process 800 includes providing information associated with the BPL estimation of the current subject.

Although FIG. 8 shows example blocks of process 800, in some implementations, process 800 may include additional blocks, fewer blocks, different blocks, or differently arranged blocks than those depicted in FIG. 8. Additionally, or alternatively, two or more of the blocks of process 800 may be performed in parallel.

Figure 9:
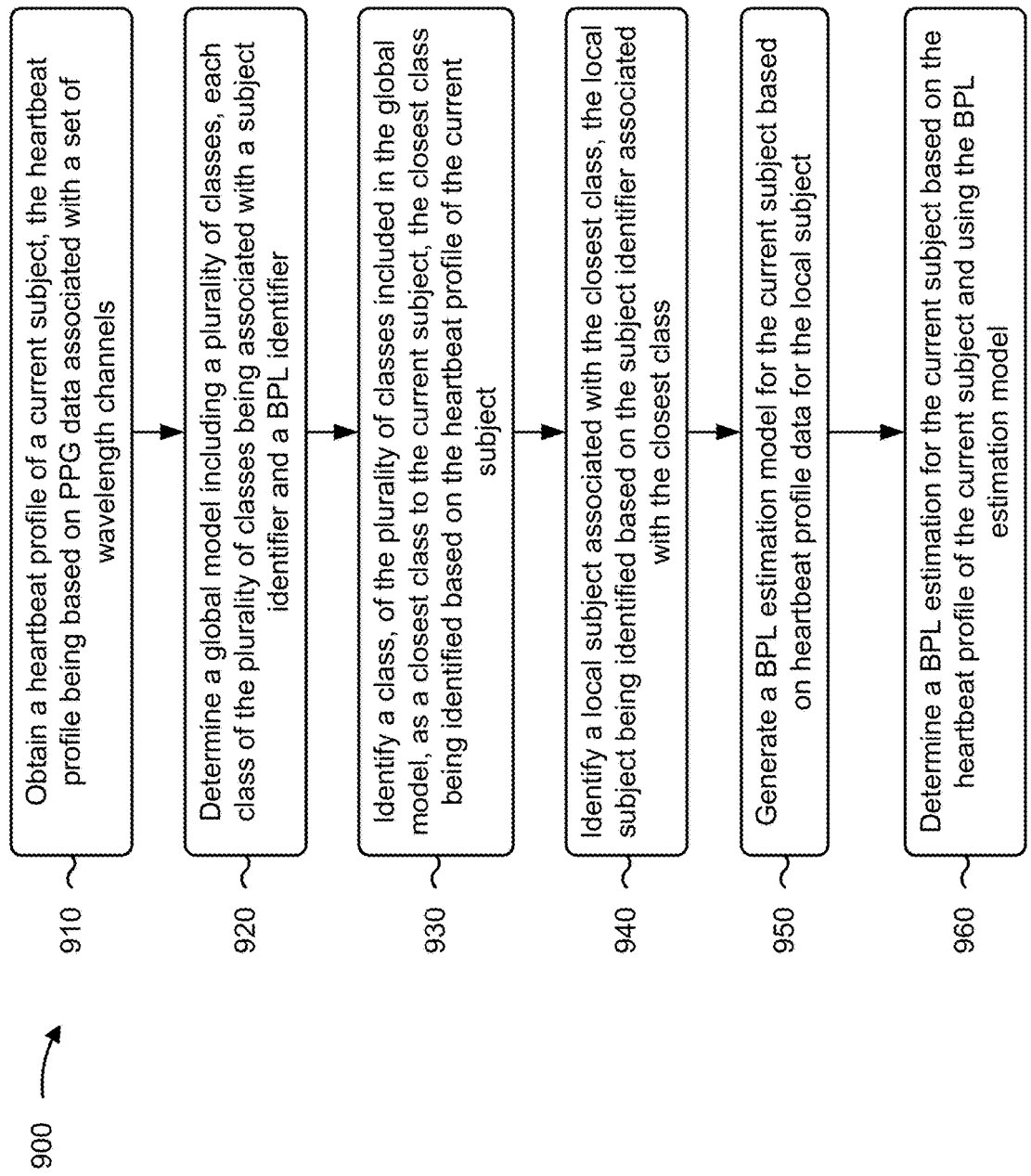

FIG. 9 is a flow chart of an example process 900 for determining a BPL estimation based on PPG data, as described herein. In some implementations, one or more process blocks of FIG. 9 may be performed by an estimation device (e.g., estimation device 510). In some implementations, one or more process blocks of FIG. 9 may be performed by another device or a group of devices separate from or including the estimation device, such as a multispectral sensor device (e.g., multispectral sensor device 505).

As shown in FIG. 9, process 900 may include obtaining a heartbeat profile of a current subject, the heartbeat profile being based on PPG data associated with a set of wavelength channels (block 910). For example, the estimation device (e.g., using processor 620, memory 630, storage component 640, input component 650, output component 660, communication interface 670, and/or the like) may obtain a heartbeat profile of a current subject, the heartbeat profile being based on PPG data associated with a set of wavelength channels, as described above.

As further shown in FIG. 9, process 900 may include determining a global model including a plurality of classes, each class of the plurality of classes being associated with a subject identifier and a BPL identifier (block 920). For example, the estimation device (e.g., using processor 620, memory 630, storage component 640, input component 650, output component 660, communication interface 670, and/or the like) may determine a global model including a plurality of classes, each class of the plurality of classes being associated with a subject identifier and a BPL identifier, as described above.

As further shown in FIG. 9, process 900 may include identifying a class, of the plurality of classes included in the global model, as a closest class to the current subject, the closest class being identified based on the heartbeat profile of the current subject (block 930). For example, the estimation device (e.g., using processor 620, memory 630, storage component 640, input component 650, output component 660, communication interface 670, and/or the like) may identify a class, of the plurality of classes included in the global model, as a closest class to the current subject, the closest class being identified based on the heartbeat profile of the current subject, as described above.

As further shown in FIG. 9, process 900 may include identifying a local subject associated with the closest class, the local subject being identified based on the subject identifier associated with the closest class (block 940). For example, the estimation device (e.g., using processor 620, memory 630, storage component 640, input component 650, output component 660, communication interface 670, and/or the like) may identify a local subject associated with the closest class, the local subject being identified based on the subject identifier associated with the closest class, as described above.

As further shown in FIG. 9, process 900 may include generating a BPL estimation model for the current subject based on heartbeat profile data for the local subject (block 950). For example, the estimation device (e.g., using processor 620, memory 630, storage component 640, input component 650, output component 660, communication interface 670, and/or the like) may generate a BPL estimation model for the current subject based on heartbeat profile data for the local subject, as described above.

As further shown in FIG. 9, process 900 may include determining a BPL estimation for the current subject based on the heartbeat profile of the current subject and using the BPL estimation model (block 960). For example, the estimation device (e.g., using processor 620, memory 630, storage component 640, input component 650, output component 660, communication interface 670, and/or the like) may determine a BPL estimation for the current subject based on the heartbeat profile of the current subject and using the BPL estimation model, as described above.

Process 900 may include additional implementations, such as any single implementation or any combination of implementations described below and/or in connection with one or more other processes described elsewhere herein.

In some implementations, generating the BPL estimation model comprises selecting at least two classes, associated with the local subject, to be used for generating the BPL estimation model for the current subject, the at least two classes includes the closest class and at least one other class associated with the local subject, the at least one other class being associated with a BPL identifier different from that of the closest class, and generating the BPL estimation model based on heartbeat profile data for the at least two classes associated with the local subject.

In some implementations, generating the BPL estimation model comprises determining a local subject transfer set associated with the local subject, the local subject transfer set including one or more heartbeat profiles of the local subject collected at or near a reference BPL (e.g., at the reference BPL or at a BPL closest to the reference BPL); obtaining a current subject transfer set associated with the current subject, the current subject transfer set including one or more heartbeat profiles of the current subject collected at the reference BPL; creating a transferred current subject set based on the current subject transfer set and the local subject transfer set, the transferred current subject set includes a plurality of transferred heartbeat profiles associated with the current subject, and generating the BPL estimation model based on a local subject set associated with the identified local subject, wherein the BPL estimation for the current subject is determined based on the transferred current subject set and using the BPL estimation model.

In some implementations, determining the global model comprises: obtaining a plurality of heartbeat profiles associated with a plurality of local subjects, each heartbeat profile of the plurality of heartbeat profiles is a heartbeat profile of one of the plurality of local subjects that is collected at a known BPL, and generating the global model based on the plurality of heartbeat profiles associated with the plurality of local subjects, the global model being generated using a non-linear classifier.

In some implementations, the BPL estimation includes an estimated BPL of the current subject.

Some implementations described herein provide a device (e.g., estimation device 1010, multispectral sensor device 1005, and/or the like) that provides improved PPG-based BPL estimation. In some implementations, the device generates a BPL estimation model for a current subject (i.e., a subject for which a BPL estimation is to be determined) based on heartbeat profile data for a local subject (i.e., a particular subject identified from a global model associated with multiple subjects), and determines a BPL estimation for the current subject based on a heartbeat profile of the current subject and using the BPL estimation model.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Some implementations are described herein in connection with thresholds. As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
   obtaining, by a device, a heartbeat profile of a current subject, the heartbeat profile being based on photoplethysmography (PPG) data, associated with a set of wavelength channels, collected by a multispectral sensor device that operates in a near infrared (NIR) spectrum;
   determining, by the device, a global model including a plurality of classes, each class of the plurality of classes being associated with a subject identifier and a blood pressure level (BPL) identifier;
   identifying, by the device, a class, of the plurality of classes included in the global model, as a closest class to the current subject, the closest class being identified based on the heartbeat profile of the current subject;
   identifying, by the device, a local subject associated with the closest class, the local subject being identified based on the subject identifier associated with the closest class;
   creating, by the device and to reduce bias associated with a BPL estimation, a transferred current subject set using mean difference correction (MDC),
      wherein using the MDC comprises mapping a first centroid, of a current subject transfer set that includes one or more heartbeat profiles of the current subject collected at a reference BPL as measured by a reference blood pressure monitor, and a second centroid, of a local subject transfer set that includes one or more heartbeat profiles of the local subject collected at or near the reference BPL, to a same location, and wherein the transferred current subject set includes a plurality of transferred heartbeat profiles associated with the current subject;

generating, by the device, a BPL estimation model based on a local subject set associated with the identified local subject;

providing, by the device, information associated with the transferred current subject set as input to the BPL estimation model;

receiving, by the device and as an output from the BPL estimation model, the BPL estimation for the current subject based on providing the transferred current subject set as input to the BPL estimation model; and providing, by the device and for display, information associated with the BPL estimation via a display screen of the multispectral sensor device.

2. The method of claim 1, wherein determining the global model comprises:

obtaining a plurality of heartbeat profiles associated with a plurality of local subjects,
wherein each heartbeat profile of the plurality of heartbeat profiles is a heartbeat profile of one of the plurality of local subjects that is collected at a known BPL; and generating the global model based on the plurality of heartbeat profiles associated with the plurality of local subjects.

3. The method of claim 1, wherein the global model is generated using a non-linear classifier.

4. The method of claim 1, wherein the BPL estimation model is a quantitative model generated using partial least squares regression.

5. The method of claim 1, wherein the BPL estimation includes an estimated BPL of the current subject.

6. The method of claim 1, wherein the BPL estimation model is a qualitative model generated using a classifier.

7. The method of claim 1, further comprising:

obtaining the PPG data from the multispectral sensor device in real-time or near real-time.

8. A method, comprising:

obtaining, by a device, a heartbeat profile of a current subject, the heartbeat profile being based on photoplethysmography (PPG) data that is based on full spectrum near infrared (NIR);

determining, by the device, a global model including a plurality of classes, each class of the plurality of classes being associated with a subject identifier and a blood pressure level (BPL) identifier;

identifying, by the device, a class, of the plurality of classes included in the global model, as a closest class to the current subject, the closest class being identified based on the heartbeat profile of the current subject;

identifying, by the device, a local subject associated with the closest class, the local subject being identified based on the subject identifier associated with the closest class;

creating a transferred current subject set based on a current subject transfer set that includes one or more heartbeat profiles of the current subject and a local subject transfer set that includes one or more heartbeat profiles of the local subject,
wherein the transferred current subject set includes a plurality of transferred heartbeat profiles associated with the current subject;

generating, by the device, a BPL estimation model for the current subject based on a local subject set associated with the identified local subject; and determining, by the device, a BPL estimation for the current subject based on the transferred current subject set and using the BPL estimation model.

9. The method of claim 8, wherein creating the transferred current subject set comprises:

determining the local subject transfer set, wherein the one or more heartbeat profiles of the local subject are collected at a reference BPL;

obtaining the current subject transfer set, wherein the one or more heartbeat profiles of the current subject are collected at the reference BPL; and creating the transferred current subject set based on the current subject transfer set and the local subject transfer set.

10. The method of claim 8, wherein determining the global model comprises:

obtaining a plurality of heartbeat profiles associated with a plurality of local subjects,
wherein each heartbeat profile of the plurality of heartbeat profiles is a heartbeat profile of one of the plurality of local subjects that is collected at a known BPL; and generating the global model based on the plurality of heartbeat profiles associated with the plurality of local subjects, the global model being generated using a non-linear classifier.

11. A method, comprising:

obtaining, by a device, photoplethysmography (PPG) data, associated with a set of wavelength channels, from a multispectral sensor device that operates in a near infrared (NIR) spectrum and is positioned relative to a skin surface of a current subject;

identifying, by the device and based on the PPG data, a class, of a plurality of classes included in a global model, as a closest class to the current subject;

identifying, by the device, a local subject associated with the closest class;

determining, by the device and based on identifying the local subject, a local subject transfer set associated with the local subject;

obtaining, by the device, a current subject transfer set associated with the current subject;

creating, by the device, a transferred current subject set by mapping based on the current subject transfer set and the local subject transfer set,
wherein the transferred current subject set includes a plurality of transferred heartbeat profiles associated with the current subject; and providing, by the device, information associated with the transferred current subject set as input to a blood pressure level (BPL) estimation model.

12. The method of claim 11, wherein obtaining the PPG data comprises obtaining, by the device, the PPG data from the multispectral sensor device based on requesting the PPG data from the multispectral sensor device.

13. The method of claim 11, wherein the device is an estimation device that is integrated with the multispectral sensor device.

14. The method of claim 11, wherein photoplethysmography (PPG) signals are previously collected at one or more known BPLs to provide a plurality of transferred heartbeat profiles according to a signal point calibration (multispectral sensor device) usage model.

15. The method of claim 11, wherein the plurality of transferred heartbeat profiles includes one or more heartbeat profiles collected at a reference BPL as measured by a reference blood pressure monitor.

16. The method of claim 11, wherein the plurality of transferred heartbeat profiles includes heartbeat profiles associated with two or more BPLs, and
wherein the two or more BPLs include a reference BPL and a BPL that differs from the reference BPL.

17. The method of claim 11, further comprising:
receiving, by the device and as an output from the BPL estimation model, a BPL estimation for the current subject based on providing the transferred current subject set as input to the BPL estimation model,
wherein the BPL estimation includes a categorical output associated with the current subject,
wherein the categorical output includes one of:
an indication of whether a BPL of the current subject has increased, decreased, or is unchanged, or
an indication of whether the current subject is in one of a hypotension state, a normal state, a prehypertension state, a hypertension stage 1, a hypertension stage 2, or a hypertensive crisis; and
providing information associated with the BPL estimation for display.

18. The method of claim 11, wherein the PPG data is obtained from the multispectral sensor device in real-time or near real-time.

19. The method of claim 11, wherein the PPG data is obtained from the multispectral sensor device on a periodic basis.

20. The method of claim 11, wherein the PPG data is collected using single-channel PPG.

* * * * *